United States Patent
Slesarev et al.

(12)

(10) Patent No.: US 6,281,191 B1
(45) Date of Patent: *Aug. 28, 2001

(54) COMPOSITIONS AND METHODS FOR TREATING HEPATITIS-C

(76) Inventors: Vladimir I. Slesarev, 2501 E. Sherman Ave. Apt. 427, Coeur D'Alene, ID (US) 83814; Todor Dimitrov, 144 Independence Dr., Brookline, MA (US) 02467

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/311,497

(22) Filed: May 13, 1999

Related U.S. Application Data (63) Continuation-in-part of application No. 08/999,460, filed on Dec. 29, 1997, now abandoned.

(51) Int. Cl.$^7$ .......................... A61K 38/16; A61K 35/00
(52) U.S. Cl. .................................. 514/8; 424/114
(58) Field of Search ................ 424/114; 514/8

(56) References Cited

U.S. PATENT DOCUMENTS

| | | | |
|---|---|---|---|
| 4,395,399 | 7/1983 | Ovchinnikov et al. | 424/177 |
| 4,401,659 | 8/1983 | Le Francier et al. | 424/177 |
| 4,801,578 | 1/1989 | Monsigny et al. | 514/8 |
| 5,505,204 | 4/1996 | Aston et al. | 514/8 |
| 5,605,690 | 2/1997 | Jacobs et al. | 424/134.1 |
| 5,773,011 | 6/1998 | Grudhofer | 424/278.1 |
| 5,798,358 | 8/1998 | Naki et al. | 514/254 |
| 5,840,719 | 11/1998 | Rubin et al. | 514/180 |

FOREIGN PATENT DOCUMENTS

| | | | |
|---|---|---|---|
| WO 97/18836 | 5/1997 | (JP) | A61K/38/45 |

OTHER PUBLICATIONS

Miyoshi et al 127: 44957 CA, 1997.*
Chertkova et al 101:14369C CA, 1984.*
Clemmesen J, Mol Biother 1989: 1(5):279–82 Abstract.
Chertkova A, Bullet Exper Biology and Medic 1984 Jul. 1998 pp. 57–59.
Ishibashi K, Clin Chim Acta Dec. 15, 1989; Abstract 185(3): 325–32.
Miyoshi E, Cancer Res Sep. 1, 1993, 53(17): Abstract 3899–902.
Mori S, J Gastroenterol Hepatol Jun. 1998; 13(6): Abstract 610–9.
Kubo S, Hepatogastroenterology Jul.–Aug. 2000; 47(34):1100–2 Abstract.
Matsui S, Virology Jan. 1994; 198(1):50–8 Abstract.
Campadelli–Fiume G, J Virol Sep. 1982; 43(3): Abstract 1061–71.
Ghoukhi A, J Gen Virol Dec. 1999; 80(Pt 12): Abstract 3099–107.
Flint M, Rev Med Virol Mar.–Apr. 2000; 10(2) Abstract 101–17.
Fergusson D, J Gen Virol Nov. 1998; 79: Abstract 2753–60.
Mullis KG, J Virol Nov. 1990; 64(11): Abstract 5317–23.
Nakano I, J Infect Dis Oct. 1999; 180(4): Abstract 1328–33.
Maheshwari RK, Nature Oct. 2, 1980, 287(5781): Abstract 454–6.
Aizaki H, J Interferon Cytokine Res Dec. 2000; Abstract 20(12):1111–20.
Zitzmann N, Proc Natl Acad Sci USA Oct. 12, 1999; 96(21):11878–82 Abstract.
Kirillicheva GB, Antibiot Med Biotekhnol May 1987; 32(5):362–4 Abstract.
Chertkova, A.I., et al., "Potentiation by Blastolysin of the Antirelapse Effect of Cyclophosphamide in Mice with T Cell Leukemia", Bulletin of Experimental Biology and Medicine, 1984, V98, N7, pp. 919–922.
Rouquet N., et al, Biochemical and Biophysical Research Comm., 229:27–35 (1996). (abstract).
Leist M., Gantner F., and Kunstle G., Mol. Med. 2:109–124(1996). (abstract).
Okazaki M., Hino K., Fujii K., Dig. Dis. Sci 41:2453–2458 (1996). (abstract).
Mochizuki K., Hayashi N., Hiramatsu N., Hepatology 24:1–7 (1996). (abstract).
Ando K., Hiroishi K., Kaneko T., J. Immunol. 158:5283–5291 (1997). (abstract).
Seyler et al., Inter. J. Immunopharmac., vol. 18, N6, pp. 385–392 (1992). (abstract).
Rigato O., Ujvari S., Castelo A., Salomao R., Infection 24:314–318 (1996).
Neuzil K.M., Tang Y.M., Graham., Am. J. Med. Sci., 311:201–204 (1996).
Nawashiro H., et al., J. Cere. Blood Flow and Met., 17:483–490(1997).
Park E., et al., Exp. Cell Res., 226:1–10 (1996). (abstract).
Andronova T., et al., Sov. Med. Rev.D. Imm. 4:1–63(1991).
Adeleye T.A. et al., APMSI 102:145–152(1994). (abstract).
Slesarev et al., PCT Serial No. 97/05889.

\* cited by examiner

*Primary Examiner*—Russell Travers
(74) *Attorney, Agent, or Firm*—Limbach&Limbach,LLP.; Michael R. Ward

(57) ABSTRACT

New compositions and methods for treating patients suffering from hepatitis-C, AIDS, aberrant apoptosis which include N-acetyl-D-glucosaminyl($\beta$-1-4)-N-Acetyl-muramyl-L-ananyl-D-isoglutamine (GMDP) of at least 98% purity and provided either alone, as an active ingredient of blastolysine, or in combination with an aminosugar such as N-acetyl-glucosamine(NAG). The high purity GMDP has a decreased amount immunogenic impurities and demonstrates cell protection as opposed to solely immunostimulatory effects, while a synergistic cell protective effect is exhibited when GMDP in combined with NAG. The new compositions modulate FasL mediated apoptosis while simultaneously stimulating TNF-$\alpha$ production and further selectively inhibiting TNF-$\alpha$ receptor p55 (TNFR1), providing a treatment for patients suffering from hepatitis-C, AIDS or aberrant apoptosis.

4 Claims, 9 Drawing Sheets

Fig. 9 DNA Fragmentation Test at 97.3% Purity of GMDP

COMPOSITIONS AND METHODS FOR TREATING HEPATITIS-C

RELATED APPLICATIONS

This application continues in part from pending application number 08/999,460 filed Dec. 29, 1997 now abandoned.

FIELD OF THE INVENTION

This invention relates to new compositions and methods for treating patients suffering from hepatitis-C and more particular compositions and methods for treating Fas antigen mediated apoptosis while simultaneously stimulating TNF-α production and concurrently modulating TNF-α receptor p55 (TNFR1) mediated apoptosis, providing treatment of apoptotic symptoms for patients suffering from diseases such as active viral hepatitis-C, and AIDS.

BACKGROUND OF THE INVENTION AND PRIOR ART

Homeostasis of multicellular organisms is controlled not only by proliferation and differentiation of cells but also by cell death. Physiological cell death mostly proceeds by apoptosis, a process which includes blebbing of the plasm membrane, condensation and segmentation of the nuclei and cytoplasm, extensive fragmentation of chromosomal DNA into nucleosome units, and cellular fragmentation into membrane apoptotic bodies which minimize the leakage of cellular constituents from the dying cell. Although apoptosis is necessary for normal development, pathological cell death occurs when the apoptotic process is either impaired or overactive contributing to a number of disease conditions, such as hepatitis-C, autoimmune disorders, diabetes, acute pancreatitis and numerous other disorders. Normalizing or modulating the apoptotic process; ie allowing apoptosis to carry out its important biological processes such as morphogenesis, tissue homeostasis, elimination of damaged or virally infected cells and the elimination of self-reactive clones from the immune system, would lead to therapeutic treatment for many of these degenerative diseases and disorders.

Apoptosis proceeds by two known triggering mechanisms; the Fas-antigen/ligand, and Tumor necrosis factor alpha(TNF-α)-Tumor necrosis factor receptor-1 (TNFR1) killing pathways. Molecular and cellular characterization of Fas antigen (CD95), a cell-surface protein recognized by cytotoxic monoclonal antibodies, has led to its identity as a receptor for Fas ligand (FasL). FasL binds to Fas, which results in triggering target cell apoptosis. Exaggeration of this system leads to pathological cell death and tissue destruction. Upregulating this antigen relates to many pathological situations in non-lymphoid organs, the Fas signaling pathways remain elusive. It has been shown that Fas-induced apoptosis of primary cultured hepatocytes requires an inhibitor of translation or protein kinase inhibitors, suggesting that two distinct pathways of Fas signaling exist in hepatocytes.(Rouquet N., et al., Biochem. Biophys. Res. Com. 229:27–35 (1996)).

In the liver, apoptosis is a physiological process involved in the clearance of injured cells and hemostatic control. However, in patients with viral fulminant hepatitis, or with nonacute liver disease, dramatic liver failure or secondary cirrhosis results from the death of hepatocytes, which is caused by the activation of both 55-kD tumor necrosis factor receptor (TNFR1) or CD95 (Fas/Apo-1). These receptors are independent and differentially regulated triggers of murine apoptotic liver failure (Leist M.,et al., Mol. Med. 2:109–124(1996)).

In chronic and filminant hepatitis-C, Fas expression is upregulated in the hepatocytes, especially near liver infiltrating lymphocytes. (Okazaki M., et al. Dig. Dis. Sci. 41:2453–2458 (1996)). The same correlation has been established with hepatitis-B virus infection. (Mochizuki K, et al. Hepatol. 24:1–7(1996)). (Ando K., et al., J. Immunol. 158:5283–529(1997)) studied the killing mechanism of bystander cells, zo which have upregulated Fas antigen. They found that killing of the antigen presenting sensitive cells is mediated by Fas ligand. Okazaki et al., suggests that hepatitis Fas expression is associated with persistent infection of hepatitis-C virus. Fas expression is upregulated in and the same correlation has been established by Mochizuki et al., for hepatitis-B virus infection.

It has also been shown that effective bystander killing requires intracellular contact between CTLs and target cells. TNF-α released from the CTLs mediates lysis of the bystander cells without a dose cell-cell contact. (Ando K., et al) Hepatic Fas expression was reduced significantly after treatment compared with the pretreatment values. Thus, a potential pathogenic treatment would require an antiapoptotic effect.

To date treatment of fulminant hepatitis relies mainly on orthotopic liver transplantation, which is limited by immunological complications and graft availability. Moreover, Fas mediated apoptosis occurs in hepatic allografts and is correlated with acute rejection. (Rouquet N., et al., Curr. Bio., 6:1192–1195(1996)). Thus, the task of a pathogenic treatment which unravels the Fas antigen blocking mechanism would allow for the design of an efficient treatment for apoptosis associated with viral hepatitis-C, acute liver failure and allograft rejection.

The development of biological response modifiers to increase macrophages mediated cytotoxicity by means of inducing TNF-α production and nitric oxide (NO) expression has become an area of great interest. In this respect, muramyl peptides are regarded as a most promising stimulaters. D-peptidoglycans namely N-acetyl-D-glucosaminyl-(β1-4)-N-acetylmuramyl-L-alanyl-D-isoglutamine (GMDP) have been proposed as the cytotoxic agents capable of eliminating cancer cells and/or virus infected cells. (Ovchinnikov, et al. U.S. Pat. No. 4,395,399).

Later, a considerable amount of research was done in order to increase the immunostimulatory efficacy of muramyl peptides (GMDP) by creating new compositions. The new compositions included the addition of lipopolysaccharide (LPS), polysaccharide such as polylactide, in combination with GMDP and MDP to increase macrophage mediated cytotoxidty (Seyler et al., lnt. J. Immunopharmac., Vol.18, N6.pp385–392, (1996)). Zink-proline salt was proposed to improve homogenecity of the artificial lipid impurities in GMDP. (Grubhofer, U.S. Pat. No. 5,773,011). Additional, peptide has been affixed to muramyl peptide in order to increase their immunogenicity (Le Frander et al., U.S. Pat. No. 4,401,659). Neoglucoproteins having affinity to macrophages or monocytes has also been proposed as an immunogenic component bound to muramyl peptides. (Monsigny et al., U.S. Pat. No. 4,801,578). Contrary to prior art, the present invention strives to decrease or eliminate LPS and polysacchrides. The inventors have found that decreasing levels of these components increases the newly discovered apoptosis regulating properties of GMDP. Thus the inventors have demonstrated that the purity level of the GMDP effects its ability to protect cells and modulate apoptosis. Regulating negative apoptosis, which occurs in many chronic viral infections and neurodegenerative conditions, requires an absolutely opposite task that the prior art has considered for GMDP, that is the inhibition of the cellular immunotoxicity (FAS antigen mediated by CD8 lymphocytes and macrophages) and humoral cytotoxicity (TNF-α mediated). For example, negative apoptosis is a main pathogenic pathway leading to liver necrosis and cirrhosis. Under such conditions, additional immunostimulation exerts detrimental effects with dangerous exaggeration of liver necrosis. Activated macrophages have been shown to be cytotoxic not only for isolated liver cells, but also in eight patients with hepatitis (Mizugoshi et al., Hepatogastroenterology, 1981;28:250–253). Moreover, the only treatment for hepatitis-C (based on the conventional strategy of macrophages stimulation by Interferons) failed to provide satisfactory results in these patients. Moreover, a high percentage of these patients experienced detrimental effects of this immunostimulation with prominent toxicity. Clinical symptoms of increased fatigue, viral load, and acceleration of liver necrosis is noticed as a consequence of the powerful immunostimulator, interferons. In direct opposition to conventional hepatitis-C treatments and prior use of GMDP, the present invention is not an immune stimulator but accomplishes the task of concurrent inhibition of both TNF-α and Fas antigen mediated cytotoxicity without extensive detrimental immunostimulation.

Until now, few compositions have been proposed to regulate aberrant apoptosis. Nakai et al. developed a method of the treatment liver cirrhosis based on carbostyril derivative and acted as apoptosis regulator in the patients with liver cirrhosis (Naki et al., U.S. Pat. No. 5,798,358).

Apoptotic compositions with active agents selected from the group consisting of serotonin, caffeine, hydrocortizone, dexamethasone, dopamine, and gluquidone was proposed by Rubin et al. (U.S. Pat. No. 5,840,719). However, the presence of immunodepressive steroids can be detrimental in those patients who have chronic viral infections.

Development of an efficient cytokine blocker has also been explored but has experienced complications relating to the need to maintain their elevated level in many clinical situations.

All previous attempts in the prior art have concentrated on blocking or inhibiting apoptosis and lowering TNF-α levels or inhibiting its production. Methods of eliminating TNF-α were disclosed in U.S. Pat. No 5,605,690 to Jacobs et al. Inhibition of TNF-α production with concurrent increase in glucose levels was disclosed by Aston in U.S. Pat. No. 5,505,204.

Recent clinical and experimental data has provided compelling evidence of a much more complicated role of TNF-α in cell pathogenesis. In some ways these studies are completely contradictory to the conventional point of view that increased levels of TNF-α is harmful and leads to terminate stage of diseases.

Elevation of circulating TNF-α was protective against sepsis (Rigato O., Ujvari S., Castelo A., Salomao R., Infection; 24:314–318(1996)) and respiratory syncytial virus infection in vivo and in vitro (Neuzil KM., Tang YM., and Graham. Am. J. Med. Sci.; 311:201–204 (1996)). Even more surprising results were obtained after administration of TNF-α, known to be a mediator of apoptosis and necrosis, was found to induce a protective effect against these conditions. Pretreatment with TNF-α significantly increased the tolerance to cerebral ischemia prior to ischemic episode. (Nawashiro H, et al., L. Cereb. Blood Flow Met.;17:483–490(1997)). This apoptosis cytokine, TNF-α, inhibits anti-lgM-mediated apoptosis in Ramos cell. (Park E., et al., Exp. Cell Res.;226:1–10(1996)).

Based on the state of the prior art it can be seen that there is a considerably degree of controversy and uncertainty about the physiological role of TNF-α. All previous attempts to eliminate or inhibit TNF-α production do not reflect the precise pathogenic role of this cytokine, thus TNF-α elimination or level reduction carry potential dangers for patients due to obvious immunosuppression and undesirable anti-apoptosis properties.

According to the present invention N-acetyl-D-glucosaminyl(β-1–4)-N-Acetyl-muramyl-L-ananyl-D-isoglutamine (GMDP) is used to modulate Fas mediated apoptosis and stimulate TNF-α production and selectively inhibit its p55(TNFR1).

GMDP was also isolated during analysis of the anti-tumor drug, blastolysine, which is a lysozyme cell wall hydrolysate of Lactobacillus Bulgaricus. (U.S. Pat. No. 4,395,399) GMDP has been extensively studied in animals, demonstrating adjuvant activity, antitumor activity, low pyrogenicity, and hypnogenic effect. (Andronova T., et al., Sov. Med. Rev. Immunol.;4:1–63(1991)).

GMDP and other muramyl dipeptides have shown inhibitory effects on lipopolysaccharide (LPS) induced TNF-α, which results in preventing the toxic action of LPS during septic shock. (Adeleye T.A., et al., A.M.P.S.;102:145–152 (1994)).

GMDP has been identified in human breast milk. it also has been suggested that GMDP enters the human body after the degradation of the probiotic part of the microflora and serves as a mediator of their systemic effect which could be clinically important. (Slesarev V., et al., PCT #97/05889). For example newborns fed with human milk are rarely infected by viral hepatitis. How and why the human milk prevents the viral hepatitis remains unknown.

SUMMARY OF THE INVENTION

Accordingly, one aspect of the present invention is to provide new GMDP compositions which include GMDP at a purity range of about 98–100% and which demonstrates apoptosis modulating properties and are useful for treating patients suffering from hepatitis-c and AIDS. Applicants also propose compositions which enhance GMDP antiapoptotic activity by specifically eliminating immunogenic impurities from GMDP, thus decreasing the compounds ability to stimulate macrophages mediated cytotoxicity.

Another aspect of the present invention is to provide new compositions of GMDP in combination with N-acetylglucosamine (and other glucosamines) which combination demonstrates synergistic antiapoptotic effect and are useful for treating patients suffering from hepatitis-C and/or AIDS.

Another aspect of the present invention is provide compositions useful for treating patients suffering from hepatitis-C, which compositions indude GMDP with a purity range of about 98–100% and administered either alone or in combination with glucosamines such as N-acetylglucosamine and or provide as an active ingredient of blastolysine. The therapeutic compositions are administered in a suitable pharmaceutical formulation.

Another aspect of the present invention indudes methods of modulating both TNF-α and Fas mediated apoptosis, by inhibiting the Fas antigen killing pathway, stimulating TNF-α production while concurrently inhibiting TNFR1 receptor by administering GMDP in a purity range of about 98–100% either alone or in combination with N-acetylglucosamine or as an active ingredient of blastolysine.

Still another aspect of the present invention includes methods of protecting a wide variety of mammalian cells including, human hepatocytes, insulin producing cells, and CD4+ lymphocytes from Fas ligand mediated cell lysis by administering GMDP either alone or in combination with N-acetylglucosamine and or provided as an active ingredient of blastolysine.

While another aspect of the present invention includes methods for enhancing GMDP antiapoptotic activity by specific eliminating of its immunogenic impurities, thus decreasing its ability to stimulate macrophages mediated cytotoxicity. And additionally, to increase the antiapoptotic activity even further by taking advantage of the newly discovered synergistic effect when GMDP is combined with N-acetylglucosamine which greatly increases the compositions antiapoptotic properties.

Another aspect of this invention is to provide a novel Fas Antigen treatment comprising administrating an effective dose of GMDP. Prevention of the cytotoxicity is achieved by exploiting the newly discovered phenomena—inhibition of binding Fas ligands Fas receptor by probiotic D-peptidoglycans, wherein the active component is GMDP, which effectively inhibits the Fas antigen killing pathways while concurrently upregulating Fas ligand on CD8+ lymphocytes.

Another aspect of this invention comprises vaginal and/or oral administration of the probiotic blastolysine, wherein the active component is GMDP, to prevent and reduce apoptosis of bystander cells (hepatocytes, and CD4+ lymphocytes) during active hepatitis-C, and HIV infection. This effect is crucial for stimulation of protective apoptosis which prevents healthy liver cells from complete destruction during viral infection. It is also the strong inhibition of Fas Ag killing pathways with concurrent modulation of TNF-α, which physiologically contributes to prevention of the liver necrosis.

In another aspect the invention comprises the administration either orally or vaginally GMDP as a Fas inhibitor, which prevents and treats the apoptosis stimulating effect of hepatitis-C virus, HIV, and Fas Ag bearing CD8+ lymphocytes.

Another aspect of the present invention indudes the prevention and treatment of liver allograft rejection.

While another aspect of the invention includes methods of enhancing GMDP cytoprotective activity by eliminating of its immunogenic impurities and increasing its purity concentration to at least 98%. In addition, the invention relates to methods for enhancing cytoprotective composition of GMDP which comprises administration to the patient an effective amount of GMDP and aminosugars. Cytoprotective synergism is achieved by composing about 50mg/kg of body weight of N-acetyl-glucosamine, D-glucosamine, N-acetyl-galactosamine, and or mannose and non cytotoxic composition of GMDP.

Oral, vaginal, and/or rectal formulations are preferred. Above mentioned aminosugars may be present as the carriers. A daily GMDP dosage in the range of from 5mg to 80mg may be found to be acceptable, with optimal range of 10–30mg per day.

DETAIL DESCRIPTION OF THE INVENTION

The examples set forth below illustrate the claimed novel uses and compositions of GMDP. The GMDP used in the examples is manufactured utilizing procedures known by those skilled in the art and as detailed by Ovchinnikov et al, U.S. Pat. No 4,395,399. Higher purity GMDP, (about 98% and higher) with decreased immunogenic compounds is accomplished by repeating the final purification steps of the known manufacturing procedures. In addition to the unexpected antiapoptotic characteristics of the higher purity GMDP a synergist effect has also been discovered when the GMDP is combined with an aminosugar, such as N-acetyglucosamine. The synergistic effect allows for the use of less GMDP, which is quite expensive, to achieve the same therapeutic (antiapoptotic) results.

EXAMPLE 1

LDH Assay of the Inhibition of Fas Antigen Mediated Apoptosis in Vitro.

The following cell lines were used for this assay: A549 (human lung carcinoma cells), A431 (human breast cancer), L929 (mouse breast cancer), human CD4+ lymphocytes taken from AIDS patient.

All cells are commercially available from ATCC. They were maintained in DME medium supplemented with 10% FCS and glutamine in $CO_2$ incubator.

Lactate dehydrogenase (LDH) assay

Cells were seeded into 35mm Petri dishes and grown up to 70% confluency. Then they were treated with human recombinant antibodies against Fas antigen (gift from Panerva Co.) in the concentration indicated in the figures.

In cases where the cells were not spontaneously sensitive to Fas ligand induced cytolysis, cycloheximide (CHX), a powerful blocker of the protein synthesis, which sensitizes the cells to anti Fas antibodies action, was used in concentration of 25 $\mu$g/ml.

The mechanism of action for CHX is unknown, but it does not affect the TNFR1 and TNFR2. Rather, CHX blocks the synthesis of proteolytic enzymes which will eventually destroy the compounds of both the Fas antigen and the TNF death pathways and thus protect the molecules sensitive to proteolytic degradation. This leads to the accumulation of proteins and cells otherwise totally resistant to Fas antigen acquired sensitivity.

Sixteen hours after treatment, 20 $\mu$l samples of the cultured supernatants were removed and assayed for LDH release by the Cytotox 96 assay (Promega Biotech., Madison, WI.)in accordance with the manufacturer's instructions.

This methodology is based upon the fact that when cells are dying they are releasing LDH. These cells are given a substrate which will produce a color reaction and, in the presence of LDH, the reaction visibly changes color.

These samples were assayed in triplicate on an EL340 Microplate reader (Bio Tech Instruments Inc.) at 490 nm wave length. The average of these three readings was plated on the graphs (FIGS. 1, 2, 3 and 4).

Figure 1:
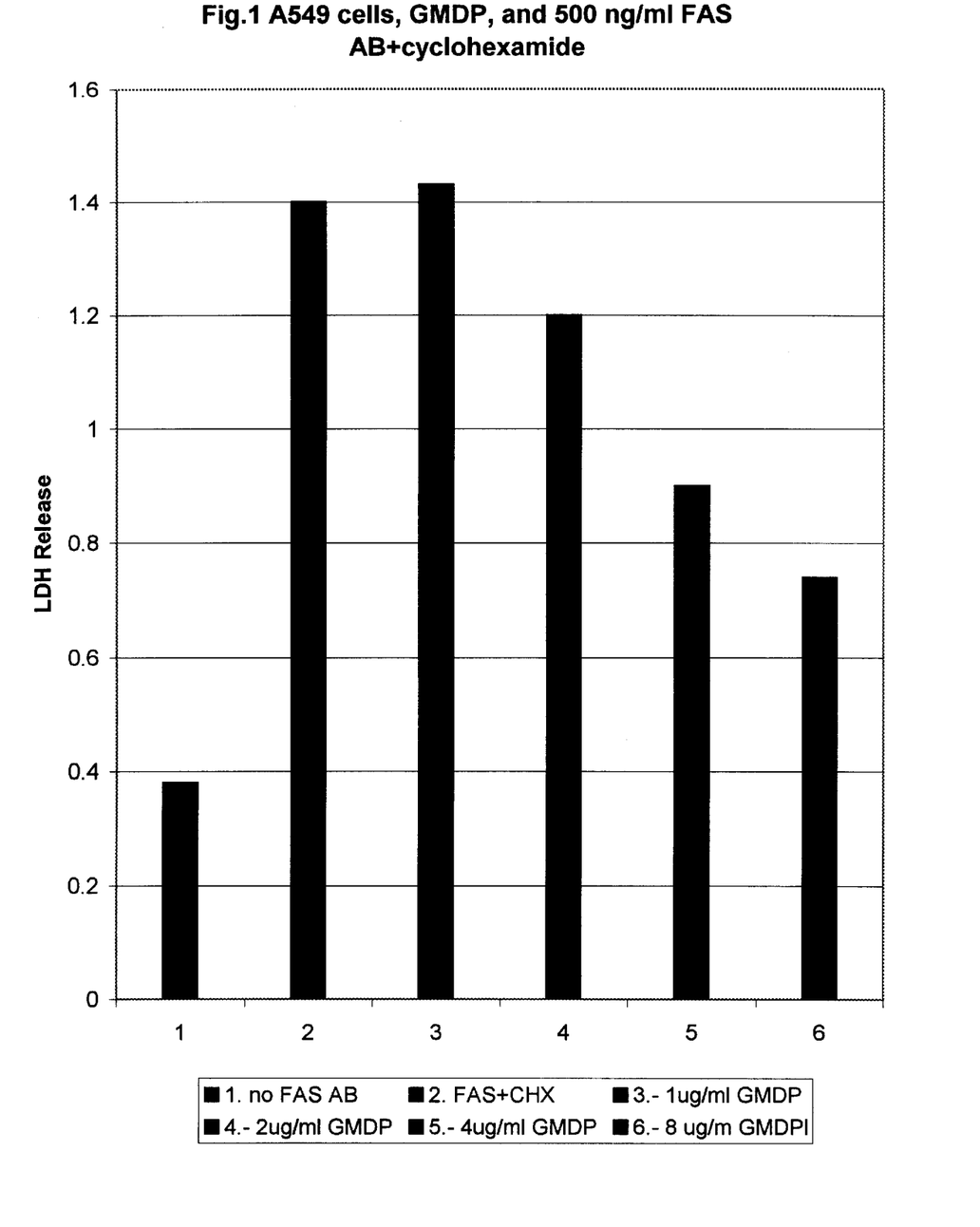
FIG. 1. GMDP inhibition of Fas mediated cytotoxicity for A549 cells.
Figure 2:
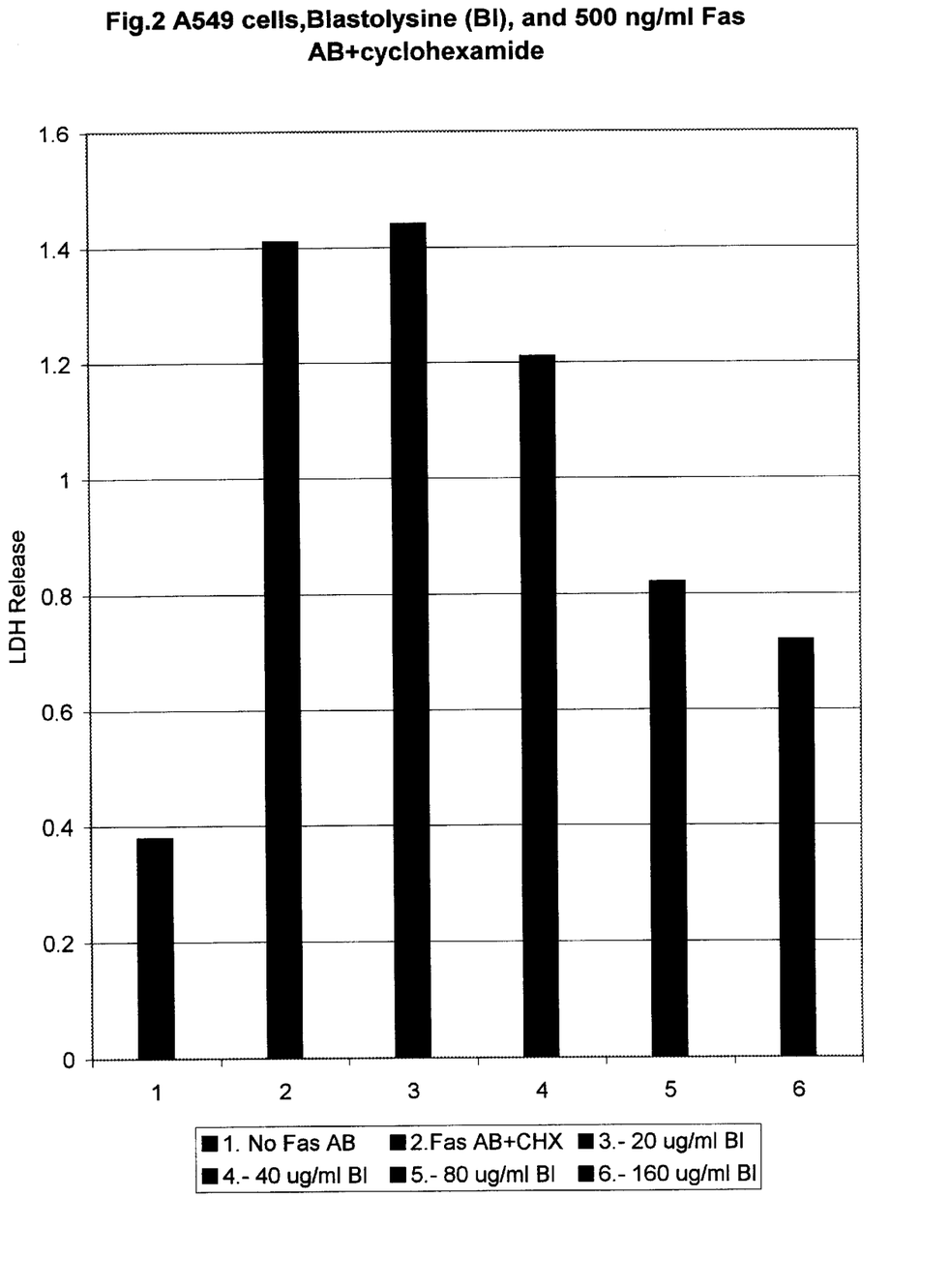
FIG. 2. Blastolysine inhibition of Fas mediated cytotoxicity for A549 cells.
Figure 3:
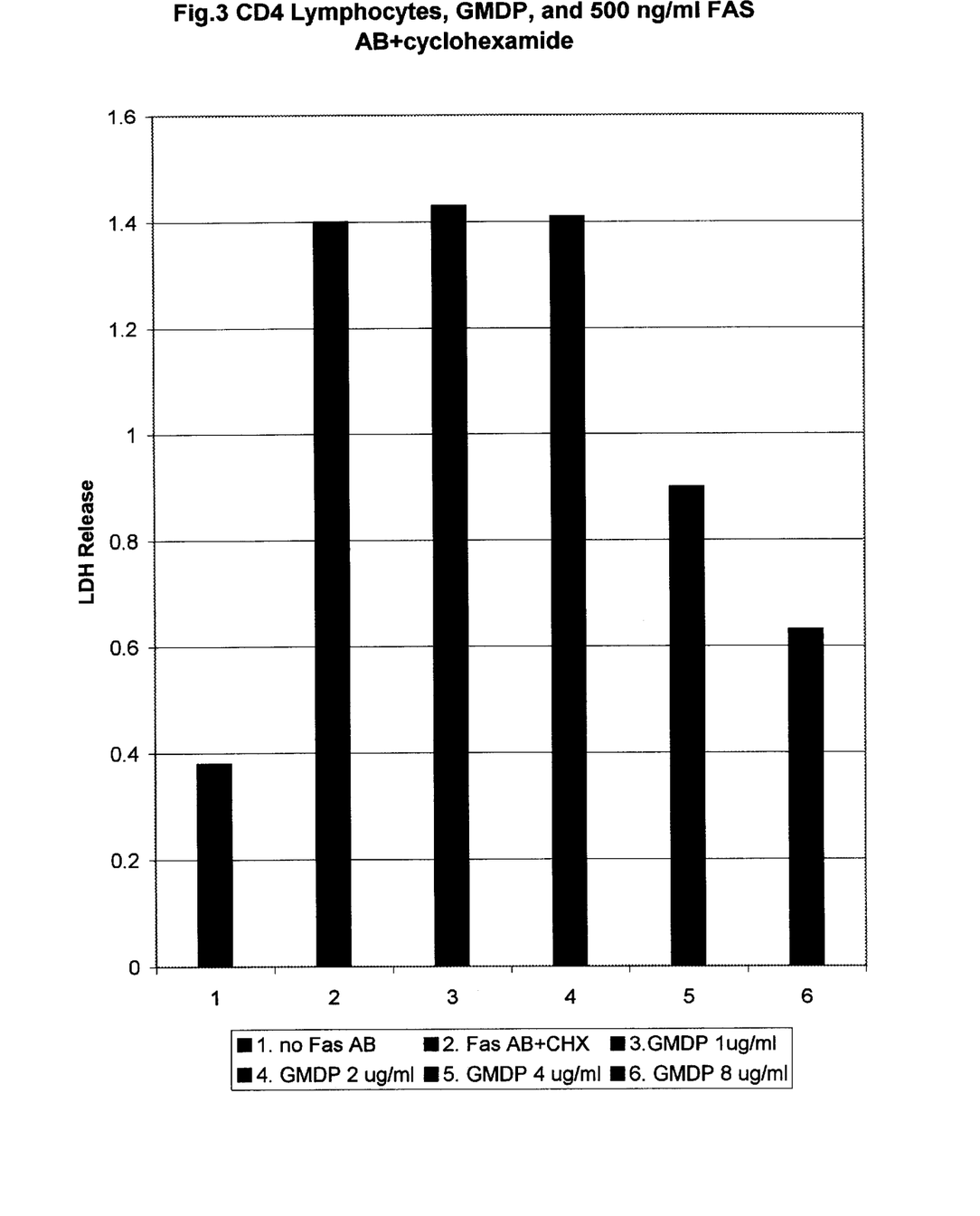
FIG. 3. GMDP inhibition of FAS mediated apoptosis for CD4 lymphocytes.
Figure 4:
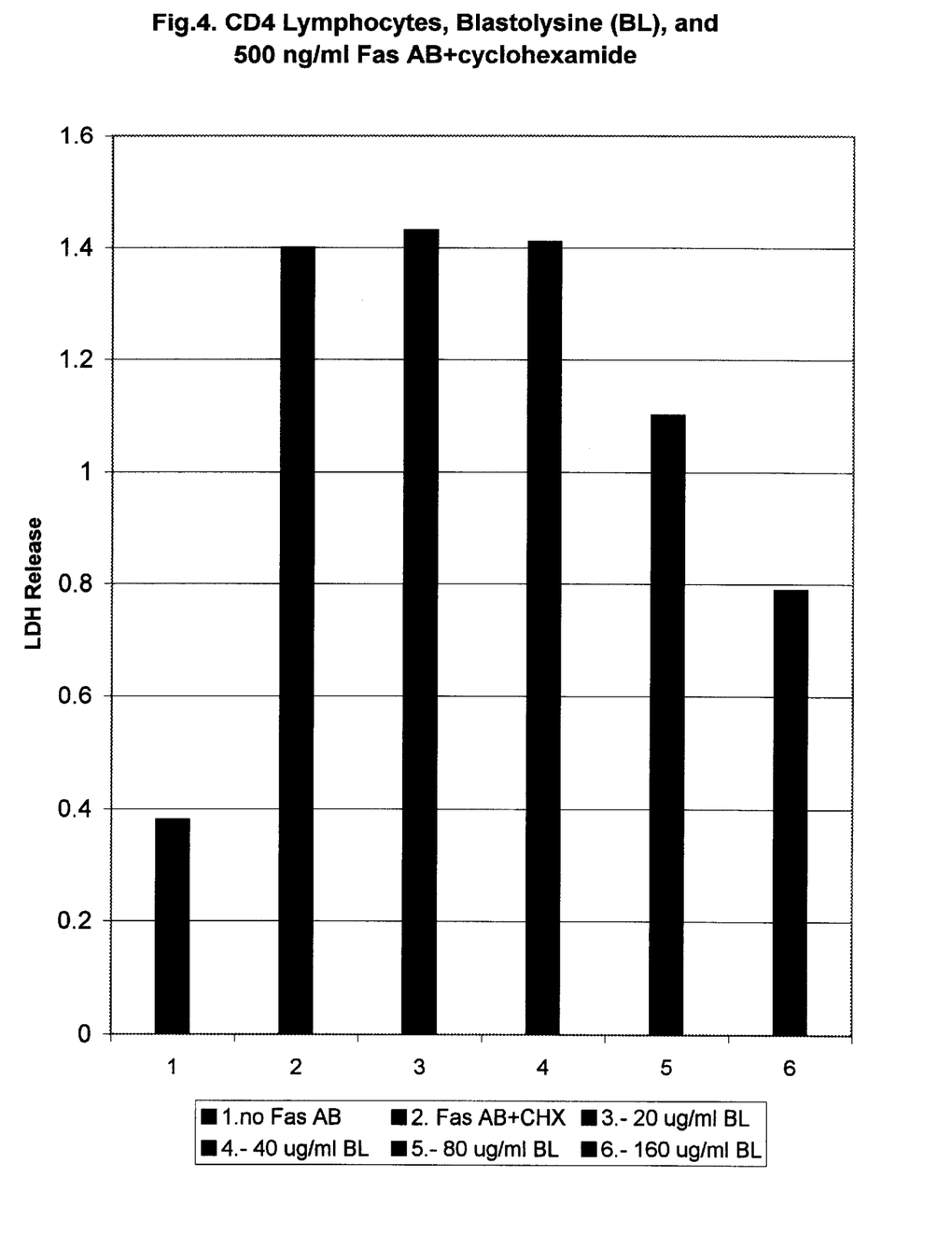
FIG. 4. Blastoylsine inhibition of Fas mediated apoptosis for CD4 lymphocytes.

One can see that the maximum inhibition of Fas Ag antibodies mediated cell lysis by GMDP was noticed on CD4 lymphocytes (72 percent reduction, as in FIG. 3).

Regarding blastolysine a 51 percent reduction was seen on the same cells (CD4 lymphocytes) at much higher concentration of 160ug/ml.

EXAMPLE 2

Comparing Antlapoptotic Effectiveness of GMDP at two different purities.

Figure 6:
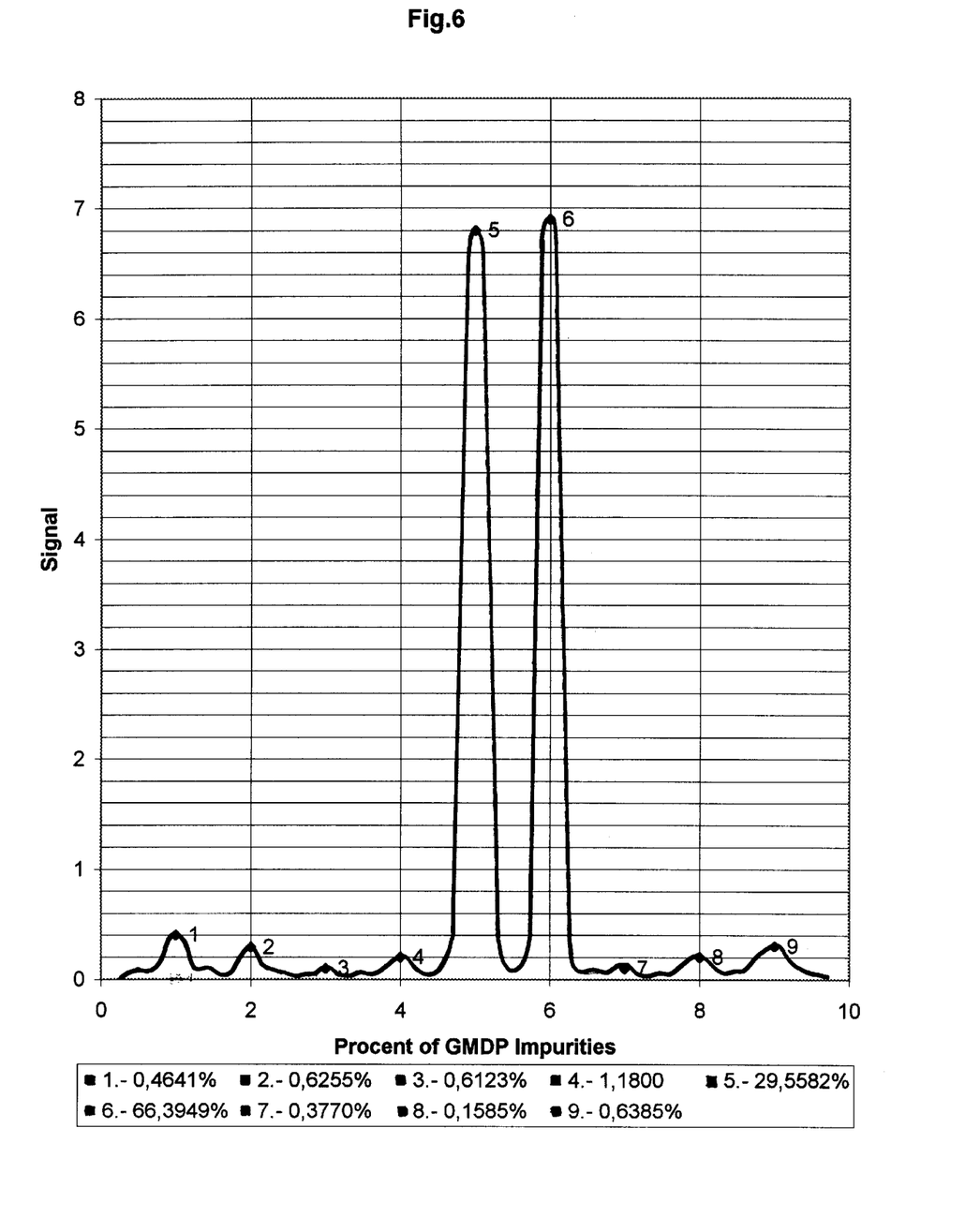
FIG. 6. HPLC spectra of GMDP composition at 97.3% purity.
Figure 7:
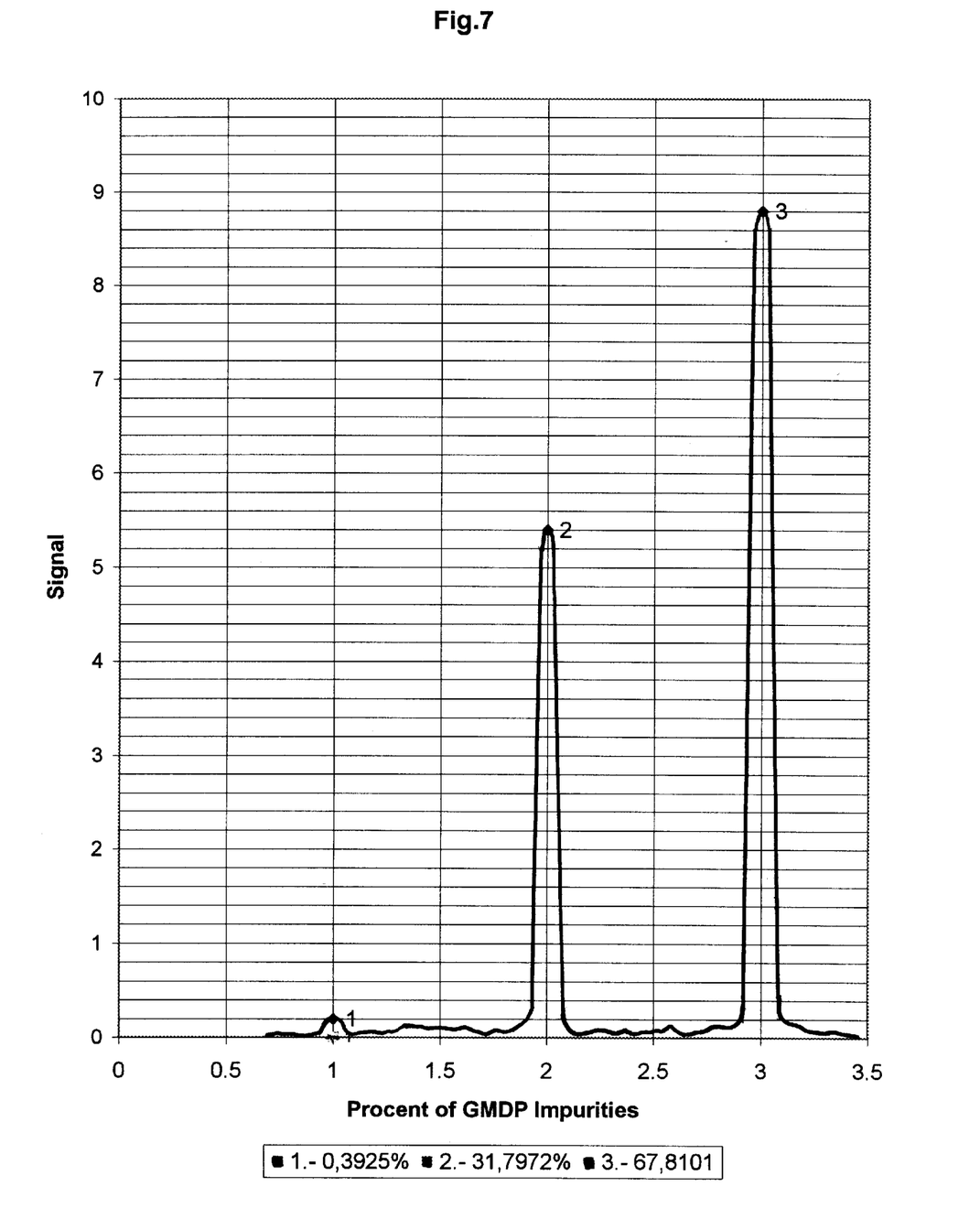
FIG. 7. HPLC spectra of GMDP composition at 98.4% purity.

Two GMDP compositions were prepared and their HPLC spectra demonstrated 1.1% difference in impurities. One can see from the spectra (FIG. 7) that the 98.4% GMDP composition does not contain liposaccharides and lactopeptides peaks that are present and numbered 7,8, an 9 on the 97.3% GMDP composition spectra (FIG. 6). The ability of these two GMDP compositions to protect cells was compared utilizing a standard DNA fragmentation procedure whereby LDH released by dying cells is measured by optic density. The LDH analysis procedure is described above.

A 549 cells (human small cell lung carcinoma) were utilized for the DNA fragmentation test and treated with GMDP 1 ug/ml and with GMDP 2 ug/ml for 2 hours and then treated with human TNF-α (Sigma Corp., St. Louis, Mo.).

Figure 8:
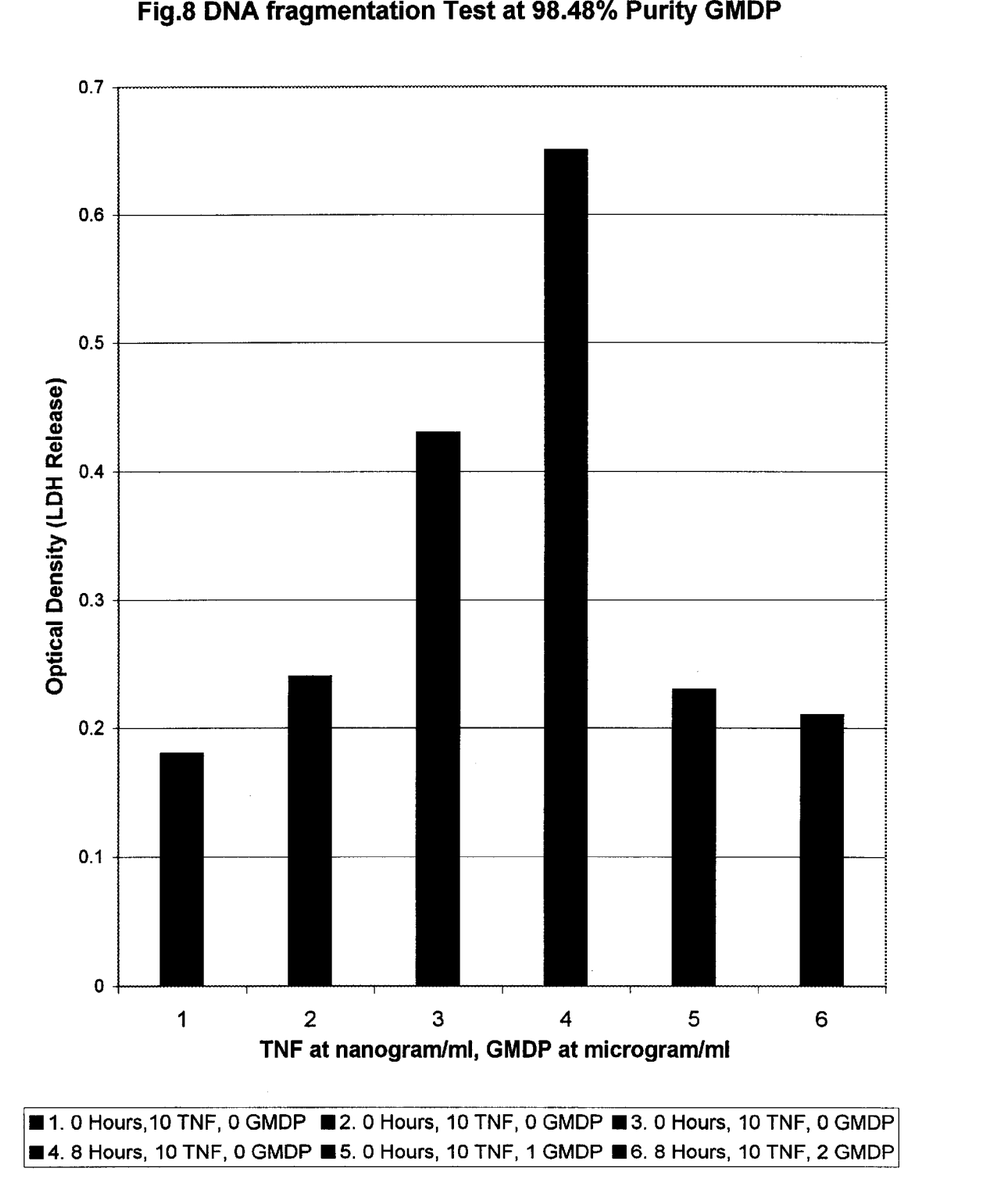
FIG. 8. DNA fragmentation test at 98.4% purity of GMDP.
Figure 9:
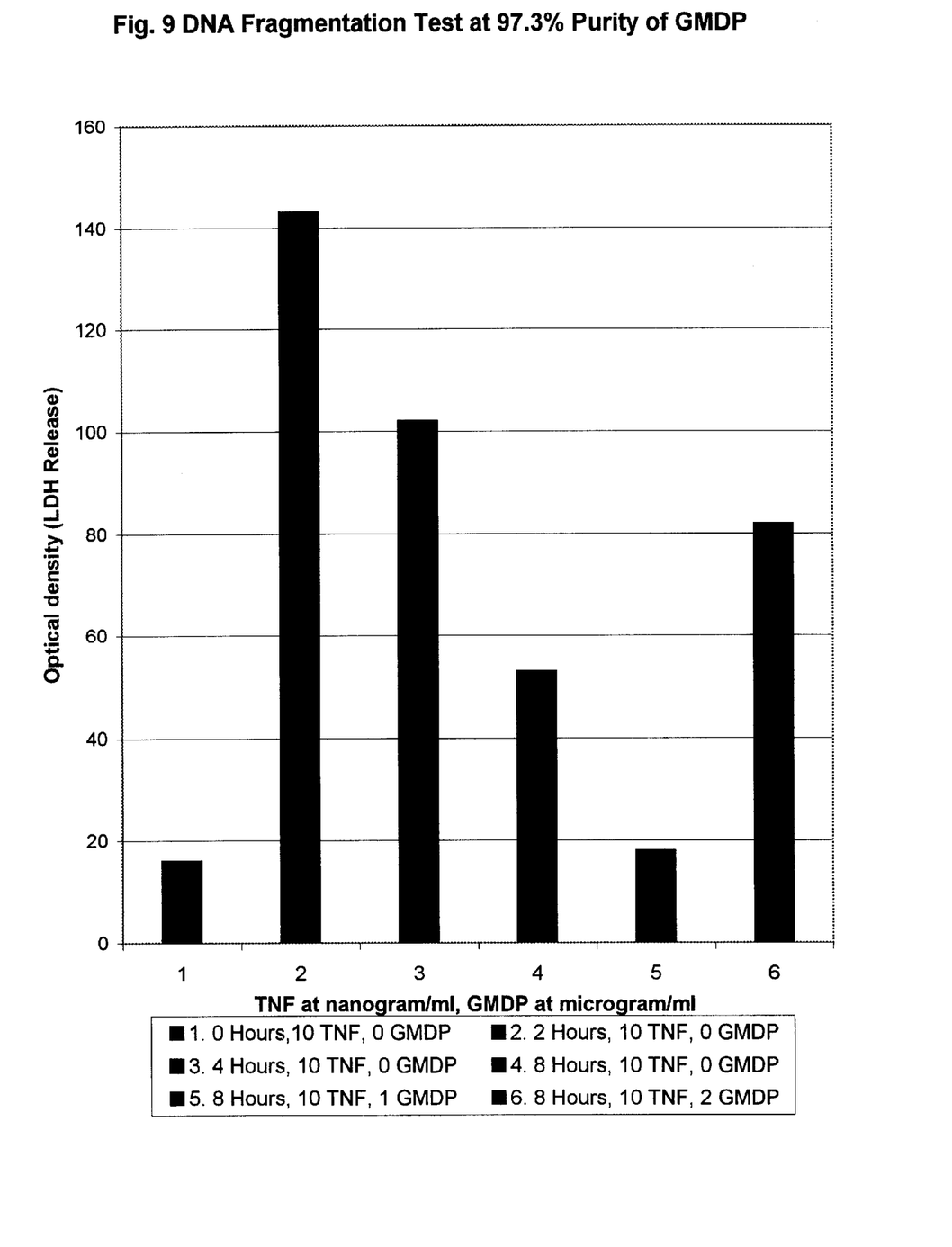
FIG. 9. DNA fragmentation test at 97.3% purity of GMDP.

FIGS. 8 and 9 are plots of the optical density measurements of two different scans each with six samples utilizing the DNA fragmentation procedure. FIG. 8 reports the results using the 97.3% purity GMDP while FIG. 9 reports the results using the 98.4% purity GMDP. TNF-α levels were 10 nanograms/ml for all samples, while samples 1–4 contained no GMDP, sample 5 contained 1 μg/mi GMDP and sample 6 contained 2 μg/ml GMDP. Sample 1 was analyzed after 0 hours, sample 2 analyzed after 2 hours, sample 3 analyzed after 4 hours, while samples 4, 5, and 6 were analyzed after 8 hours. Accordingly, only samples 5 and 6 from each scan measure cell protection after 8 hours. As can be readily seen from these sample results that the cells exposed to GMDP of about 98.3% purity have an optical density value of less than ½ of the optical density measured for the cells exposed to GMDP of about 97.3% purity. In other words, the higher purity GMDP drastically increases cell protection and antiapoptotic activity.

These results are unexpected, especially in view of the prior art attempts to increase and/or add lipopolysacchrides to GMDP for immunostimulatory purposes. The results are also unexpected in light of the relatively small increase in purity (about 1%) notwithstanding the small purity increase the difference in utility is drastic, especially for antiapoptotic purposes.

EXAMPLE 3

GMDP Treatment of Active Hepatitis C

Twelve patients in the active stage of hepatitis-C were selected for this study. The study group consisted of eight females and four males between 36 and 57 years of age. All patients had not responded to previous treatment with interferons. Quantitatively PCR (RNA) test revealed viral load in a range of 500×1000–44700×1000 particles/μl. All of the patients suffered from fatigue, nausea and their blood test revealed an elevated activity of AST, APT, GGTP and LDH. In three patients liver biopsy examination revealed mild necrosis, fibrosis with 10–16% cirrhosis.

Blastolysine and N-acetyl-glucosaminyl-muramyldipeptide (GMDP 98.4% purity) supplied in powered form is a semisynthetic D-peptidoglycan identical to the wall fragment of lactobacilli bulgaricus. The control powder contained vegetable oil, corn syrup solids, and lactose. Quality control (to check for product identity and purity) was done by HPLC through comparisons with those obtained from reference samples from Sigma Corp, St Louis, Mo.

The GMDP powder was diluted with 10 ml sterile distilled water. The daily GMDP dosage ranged from 0.1–0.5 mg/kg of the patient's body weight for blastolysine 80–120mg/kg of body weight.

Statistical analysis were done with Epi-Info Statistical Package (Center for Disease Control and Prevention, Atlanta, Ga.) with two way comparison by the Fischees exact test (two tailed).

Eleven patients were orally administered GMDP at dosage of 0.5–1 mg/kg daily in a water solution for one or two months. One patient with 44000×1000 viral load and early liver cirrhosis was treated for one year. GMDP at dosage of 0.1–0.5 mg/kg daily was administered to 11 patients. No patients were withdrawn early from this study.

During the follow up period, the overall clinical conditions of all patients treated with GMDP was improved. No patients experienced toxic effects. Fatigue and nausea completely subsided after first week in all patients who had these symptoms of tumor toxicity before treatment. In one patient with high levels of free iron, GMDP treatment resulted in full normalization of this test. After the first three weeks of treatment, serum HPC RNA test revealed two-three fold reduction of viral load in all patients.

In parallel, the beneficial effect on AST and APT activity was observed in 7 patients who had elevated level of these enzymes. GMDP decreased LDH and GGTP activity in the rest of the patients by 34% (6) in all 7 patients who had elevated level of this enzyme. Lowering effect on alkaline phosphates activity also was noticed in one patient with previously elevated level of this liver enzyme. Reduction in bilirubin concentration by 19%(3) was observed in 2 patients with its elevated level. Results of two months followup test were expressed as percentage of change in viral load levels from pretreatment values.

In parallel, follow-up biopsy was done in all three patients who had it before. In one patient pathology examination revealed no sign of previous necrosis and cirrhosis at end of one year treatment. In two patients with diagnosed mild necrosis and fibrosis follow up biopsy demonstrated mild lymphoid cell infiltration in portal area while no necrosis or fibrotic change was detectable.

EXAMPLE 4

Synergistic Effect of the Combination GMDP+ NAG

Figure 5:
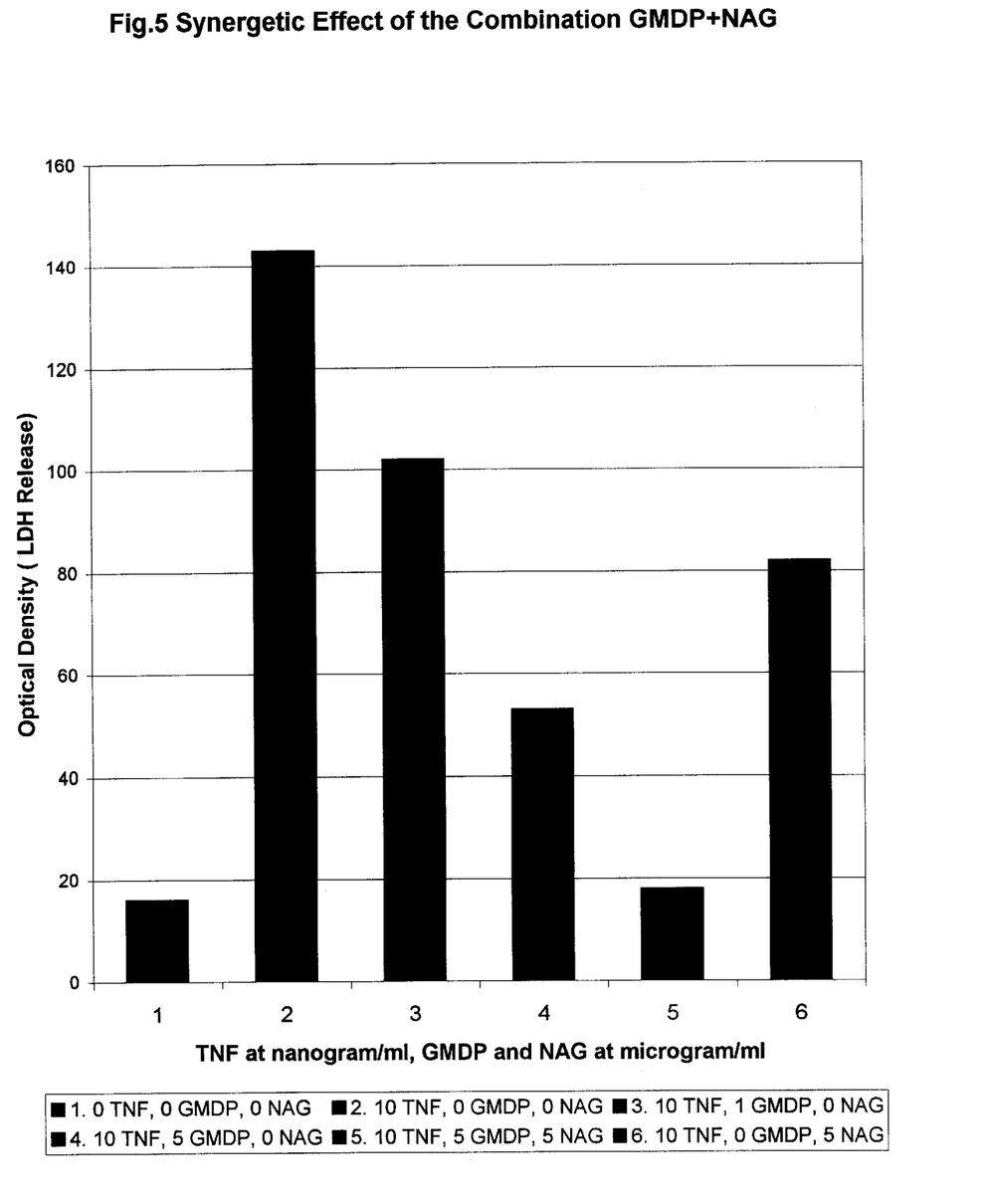
FIG. 5. Synergistic effect of the Combination GMDP+NAG.

The synergistic effect of combining GMDP with N-acetylglucosamine (NAG) was evaluated utilizing a nuclear fragmentation technique.(fragmented cell count on the "y" axis) summarized on FIG. 5.

A 549 cells (human small cell lung carcinoma) were treated with various concentrations of GMDP, NAG, and TNF-α in six different samples. The cells were then fixed by methanol with DAPl (Sigma) at 1 ug/ml for 8 min at −20° C. and then for 2 min at the same temperature with no DAPl. The entire procedure was accomplished on cover slips in 35 mm petri dishes and after fixation the cover slips were mounted on slides and observed under UV immersion microscope. The nuclei were fragmented in apoptotic cells and intact in non-apoptotic (protected) cells.

Sample 1 was a control which contained no TNF, GMDP or NAG. Sample 2 contained 10 nanograms/ml of TNF-α, no GMDP and no NAG. Sample 3 contained 10 nanograms/ml TNF-α, 1 µg/ml GMDP, and no NAG. Sample 4 contained 10 nanograms/ml TNF-α, 5 µg/ml GMDP, and no NAG. Sample 5 contained 10 nanograms/ml TNF-α, 5 µg/ml GMDP, and 5 µg/ml NAG. Sample 6 contained 10 nanograms/ml TNF-α, no GMDP, and 5 µg/ml NAG.

The actual cell counts were taken from the six samples and plotted. Sample 2 illustrates almost complete cellular death while sample 1 illustrates no cell death. As can be easily seen, maximum cellular protection is achieved with the combination GMDP and NAG. An almost three fold increase in cell protection is demonstrated for the combination in comparison with GMDP alone and almost four times the protection than with NAG alone.

These surprising results illustrate that GMDP in combination with the aminosugar NAG has a synergistic effect in relation to cell protection, antiapoptosis.

We claim:

1. A method for treating Hepatitis C in a patient having a detectable hepatitis C viral load, by administering blastolysin which contains GMDP as an active ingredient in a dosage range of about 0.1–1,5 mg/kg of body weight.

2. The method of claim 1 wherein the blastolysine is administered in combination with one or more aminosugars in a dosage range of about 20–80 mg/kg of body weight.

3. The method of claim 1 wherein the blastolysine is administered in combination with N-acetylglucosamine a dosage range of about 20–80 mg/kg of body weight.

4. The method of claim 1 wherein the blastolysine is administered in combination with one or two aminosugars in a dosage range of about 20–80 mg/kg of body weight, the aminosugars selected from a group consisting of:

N-acetylglucosamine

D-glucosamine.

* * * * *